US011856308B2

(12) United States Patent
Osawa

(10) Patent No.: US 11,856,308 B2
(45) Date of Patent: Dec. 26, 2023

(54) IMAGE SENSOR, ENDOSCOPE AND CONTROL DEVICE

(71) Applicant: OLYMPUS CORPORATION, Hachioji (JP)

(72) Inventor: Masato Osawa, Hachioji (JP)

(73) Assignee: OLYMPUS CORPORATION, Hachioji (JP)

( * ) Notice: Subject to any disclaimer, the term of this patent is extended or adjusted under 35 U.S.C. 154(b) by 351 days.

(21) Appl. No.: 17/420,775

(22) PCT Filed: Jan. 9, 2019

(86) PCT No.: PCT/JP2019/000397
§ 371 (c)(1),
(2) Date: Jul. 6, 2021

(87) PCT Pub. No.: WO2020/144777
PCT Pub. Date: Jul. 16, 2020

(65) Prior Publication Data
US 2022/0070403 A1   Mar. 3, 2022

(51) Int. Cl.
*H04N 25/71* (2023.01)
*A61B 1/00* (2006.01)
*H04N 25/75* (2023.01)

(52) U.S. Cl.
CPC ....... *H04N 25/745* (2023.01); *A61B 1/00006* (2013.01); *A61B 1/00009* (2013.01);
(Continued)

(58) Field of Classification Search
CPC .................................................. H04N 25/745
(Continued)

(56) References Cited

U.S. PATENT DOCUMENTS

| 2007/0139521 A1 | 6/2007 | Takahashi |
| 2014/0285645 A1 | 9/2014 | Blanquart et al. |
| 2019/0280707 A1 | 9/2019 | Hiraide et al. |

FOREIGN PATENT DOCUMENTS

| JP | 2007-159991 A | 6/2007 |
| JP | 2016-520341 A | 7/2016 |

(Continued)

OTHER PUBLICATIONS

International Search Report dated Apr. 16, 2019, issued in counterpart application No. PCT/JP2019/000397, w/English translation (4 pages).
(Continued)

*Primary Examiner* — Joel W Fosselman
(74) *Attorney, Agent, or Firm* — WHDA, LLP

(57) ABSTRACT

An image sensor includes: a pixel unit including pixels configured to generate a first signal corresponding to an amount of received light, and output the first signal; an AD converter configured to convert the first signal into a digital second signal by performing AD conversion processing for the first signal, and output the second signal; a transmitter/receiver configured to transmit and receive, in a time division manner, transmission data including at least the second signal in a first period, and reception data input from an outside in a second period; and a first generator configured to generate a first clock signal synchronized with the clock edge included in the reception data. The transmitter/receiver is configured to switch between the first period and the second period every horizontal line in the pixel unit, and transmit and receive the transmission data and the reception data in a time division manner.

8 Claims, 7 Drawing Sheets

(52) U.S. Cl.
CPC ...... *A61B 1/00013* (2013.01); *A61B 1/00117* (2013.01); *H04N 25/75* (2023.01)

(58) Field of Classification Search
USPC ......................................................... 348/308
See application file for complete search history.

(56) References Cited

FOREIGN PATENT DOCUMENTS

| JP | 2016520341 | * | 7/2016 |
|---|---|---|---|
| WO | 2014/145246 A1 | | 9/2014 |
| WO | 2018/116540 A1 | | 6/2018 |

OTHER PUBLICATIONS

Written Opinion dated Apr. 16, 2019, issued in counterpart application No. PCT/JP2019/000397 (7 pages).

* cited by examiner

IMAGE SENSOR, ENDOSCOPE AND CONTROL DEVICE

FIELD

The present disclosure relates to an image sensor, an endoscope and a control device which generate image data by capturing an image of a subject.

BACKGROUND

Heretofore, in an endoscope system, there has been known a technique for performing, by using a clock data recovery (CDR) circuit of a camera unit, transmission/reception of output data in a predetermined frame cycle via an input/output pad provided in an image sensor (refer to Patent Literature 1). In this technique, the image sensor includes: a rolling read state of outputting image data via the input/output pad; a service state of outputting non-image data via the same; and a configuration state of causing the image sensor to receive, via the same, command data including a signal for recovering an error. At timing of the configuration state in this predetermined frame cycle, the image sensor locks a clock signal by the CDR circuit of the camera unit, which is included in the output data.

CITATION LIST

Patent Literature

Patent Literature 1: JP 2016-520341 A

SUMMARY

Technical Problem

However, in Patent Literature 1 mentioned above, since the timing of the configuration state is present every frame, a signal for recovering an error must be awaited until a next frame when the error occurs in data due to invasion of a disturbance noise by use of an electric scalpel, and the like. Therefore, there has been a problem that data in an entire frame where the error occurs is lost.

The present disclosure has been made in view of the above. It is an object of the present disclosure to provide an image sensor, an endoscope and a control device which are capable of rapidly recovering data even when an error occurs in the data.

Solution to Problem

To solve the above-described problem and achieve the object, an image sensor according to the present disclosure includes: a pixel unit including a plurality of pixels arranged in a two-dimensional matrix, each of the plurality of pixels being configured to generate, by receiving light, a first signal corresponding to an amount of the received light, and output the first signal; an AD converter configured to convert the first signal output from each of the plurality of pixels into a digital second signal by performing AD conversion processing for the first signal, and output the second signal; a transmitter/receiver configured to transmit and receive, in a time division manner, transmission data including at least the second signal in a first period, and reception data input from an outside in a second period, the reception data including a setting signal and a clock recovery symbol having a clock edge for detecting transition timing of data; and a first generator configured to generate a first clock signal synchronized with the clock edge included in the reception data, wherein the transmitter/receiver is configured to switch between the first period and the second period every horizontal line in the pixel unit, and transmit and receive the transmission data and the reception data in a time division manner.

Moreover, in the above-described image sensor according to the present disclosure, the transmitter/receiver is configured to transmit and receive the transmission data and the reception data in a time division manner via one input/output pad.

Moreover, the above-described image sensor according to the present disclosure further includes a second generator configured to generate, based on the first clock signal, a second clock signal for driving the pixel unit and the AD converter at fixed reference timing, and output the second clock signal to the pixel unit and the AD converter.

Moreover, in the above-described image sensor according to the present disclosure, the first generator includes: a phase frequency comparator configured to output an input signal indicating a comparison result of comparing the first clock signal and the reception data with each other; a charge pump unit configured to, based on the input signal input from the phase frequency comparator, adjust a voltage of the input signal and output the input signal; a loop filter unit configured to smooth the voltage of the input signal input from the charge pump unit and output the input signal; and a first voltage control oscillator configured to generate and output the first clock signal having a frequency corresponding to the voltage of the input signal input from the loop filter unit.

Moreover, in the above-described image sensor according to the present disclosure, the first generator includes: a phase frequency comparator configured to output an input signal indicating a comparison result of comparing the first clock signal and the reception data with each other; a charge pump unit configured to, based on the input signal input from the phase frequency comparator, adjust a voltage of the input signal and output the input signal; a loop filter unit configured to smooth the voltage of the input signal input from the charge pump unit and outputs the input signal; a first voltage control oscillator configured to generate and output a third clock signal having a frequency corresponding to the input signal input from the loop filter unit; a DA converter configured to perform DA conversion processing for the third clock signal input from the first voltage control oscillator and output the third clock signal; and a second voltage control oscillator configured to generate and output the first clock signal having a frequency corresponding to a voltage of the analog third clock signal input from the DA converter.

Moreover, in the above-described image sensor according to the present disclosure, the setting signal includes a frequency control signal of the second clock signal, and the transmission data includes the second signal and a preamble signal to be output at earlier timing than the second signal.

Moreover, in the above-described image sensor according to the present disclosure, the transmission data includes an image format, and the image format has a configuration code period at least every line.

Moreover, an endoscope according to the present disclosure includes: the above-described image sensor; and an insertion portion having a distal end inserted into a subject, wherein the image sensor is provided on the distal end.

Moreover, a control device according to the present disclosure to which an endoscope is detachably connected, the endoscope including an image sensor provided on a distal end of an insertion portion insertable into a subject, includes: a transmitter/receiver configured to transmit and receive transmission data and reception data in a time division manner, wherein the transmission data passes via one transmission cable and is transmitted at least from the image sensor in a first period, the transmission data including image data, non-image data, and a clock recovery symbol having a clock edge for detecting transition timing of data, and the reception data being received by the image sensor and including a setting signal and a clock recovery symbol having a clock edge for detecting transition timing of data.

Moreover, the above-described control device according to the present disclosure further includes: a third generator configured to generate a reference clock signal serving as a reference of an operation of the control device; and a control unit configured to output the image data to a display device based on the reference clock signal and a first clock signal generated in synchronization with the clock edge included in the reception data.

Advantageous Effects of Invention

According to the present disclosure, an effect is exerted that data can be rapidly recovered even when an error occurs in the data.

DESCRIPTION OF EMBODIMENTS

Figure 1:
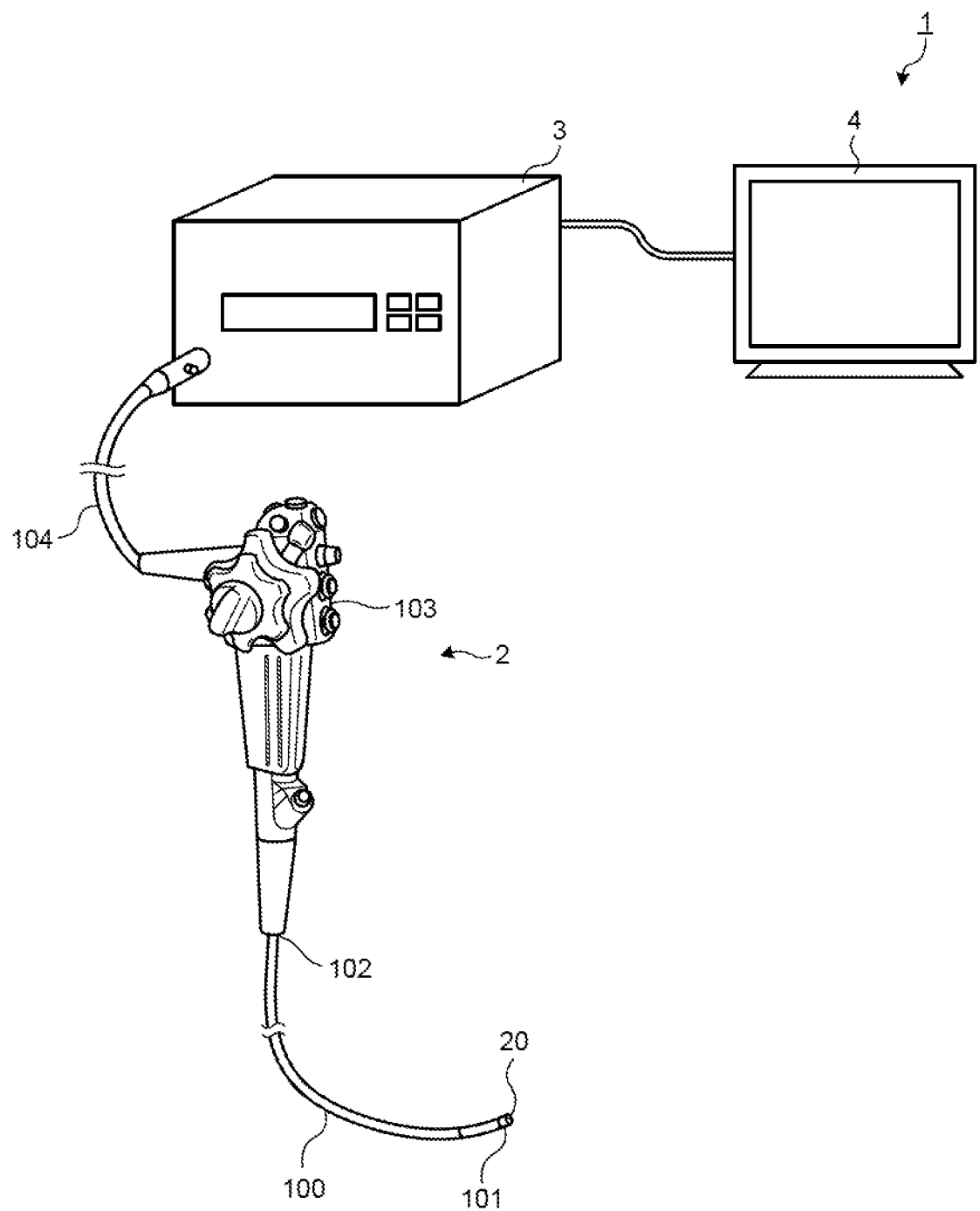
FIG. 1 is a schematic view schematically illustrating an entire configuration of an endoscope system according to a first embodiment.

A description will be given below of an endoscope system provided with an endoscope having an imaging device on a distal end portion of an insertion portion to be inserted into a subject. This endoscope system serves as a mode for embodying the present disclosure (hereinafter, this mode will be referred to as an "embodiment"). Moreover, the present disclosure is not limited by this embodiment. Further, in the description referring to the drawings, the same portions will be described while being denoted by the same reference numerals. Still further, the drawings are schematic, and it should be noted that a relationship between a thickness and width of each member, ratios of respective members, and the like are different from actual ones. Moreover, portions different in dimension and ratio from one another between the drawings are included.

First Embodiment (Configuration of Endoscope System)

FIG. 1 is a schematic view schematically illustrating an entire configuration of an endoscope system according to a first embodiment. The endoscope system 1 illustrated in FIG. 1 includes an endoscope 2, a control device 3, and a display device 4.

The endoscope 2 captures an image of an internal body of a subject by inserting, into a body cavity of the subject, an insertion portion 100 that is a part of the endoscope 2, and outputs, to the control device 3, an image signal generated by capturing the image of the internal body. On a distal end portion 101 of the insertion portion 100, the endoscope 2 is provided with an imaging device 20 that captures the image of the internal body of the subject and generates the image signal. Moreover, on a proximal end side 102 of the insertion portion 100, the endoscope 2 is provided with an operating unit 103 that receives a variety of operations regarding the endoscope 2. Further, the endoscope 2 is provided with a transmission cable 104 that extends from the operating unit 103 and is detachably connected to the control device 3. The image signal of such an in-vivo image, which is generated by the imaging device 20, passes via the transmission cable 104 having a length, for example, of several meters, and is output to the control device 3. The transmission cable 104 is composed by using a cable, an optical fiber or the like, and transmits, to the control device 3, a variety of data including the image signal generated by the imaging device 20. Moreover, the transmission cable 104 transmits a variety of data, which are transmitted from the control device 3, to the imaging device 20, and guides illumination light, which is supplied from a light source device (not illustrated), to the distal end portion 101 of the insertion portion 100 of the endoscope 2.

The control device 3 implements predetermined image processing for the variety of data input thereto via the transmission cable 104, and outputs the variety of data to the display device 4. Moreover, the control device 3 comprehensively controls the entire endoscope system 1. For example, the control device 3 performs controls to switch the illumination light emitted by the light source device (not illustrated), and to switch an imaging mode of the endoscope 2.

The display device 4 displays an image corresponding to the image signal subjected to the image processing by the control device 3. The display device 4 displays a variety of information regarding the endoscope system 1. The display device 4 is composed by using a display panel of liquid crystal or organic electroluminescence (EL), or the like.

(Main Parts of Imaging Device and Control Device)

Figure 2:
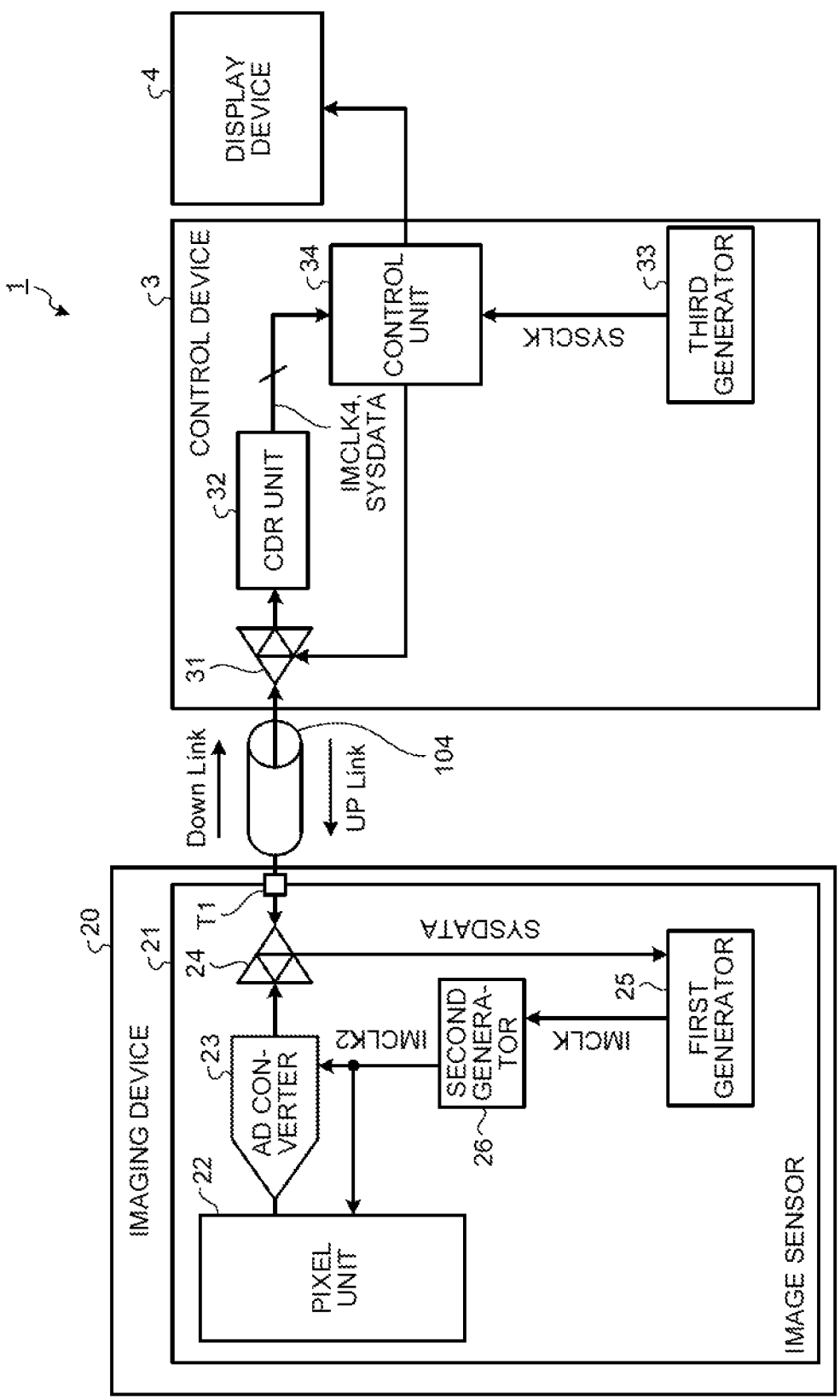
FIG. 2 is a block diagram illustrating functional configurations of main parts of an imaging device and a control device according to the first embodiment.

Next, a description will be given of functions of main parts of the imaging device 20 and the control device 3 which are mentioned above. FIG. 2 is a block diagram illustrating functional configurations of the main parts of the imaging device 20 and the control device 3.

(Configuration of Imaging Device)

First, a configuration of the imaging device 20 will be described.

The imaging device 20 illustrated in FIG. 2 includes an image sensor 21. The image sensor 21 is composed, for example, by using an image sensor of a complementary metal oxide semiconductor (CMOS) or a charge coupled device (CCD), or the like. The image sensor 21 includes at least a pixel unit 22, an AD converter 23, a transmitter/receiver 24, a first generator 25, and a second generator 26.

The pixel unit 22 is composed in such a manner that a plurality of pixels are arranged in a two-dimensional matrix. The pixel unit 22 generates a first signal (analog pixel value) corresponding to an amount of received light in such a manner that each of the plurality of pixels receives light. The pixel unit 22 outputs, to the AD converter 23, the first signal generated by each of the plurality of pixels. On the basis of a second clock signal for driving the pixel unit 22 at fixed reference timing, the second clock signal being to be input from a second generator 26 to be described later (and being hereinafter referred to as "imager clock signal IMCLK2"), the pixel unit 22 reads out the first signal from each of the plurality of pixels every horizontal line in the pixel unit 22, and outputs this readout first signal to the AD converter 23.

On the basis of the second clock signal (imager clock signal) IMCLK2 input from the second generator 26, the AD converter 23 performs AD conversion processing for the first signal input from the pixel unit 22, thereby converts the first signal into a digital second signal (digital image signal), and outputs this second signal to the transmitter/receiver 24. The AD converter 23 is composed by using such a known AD conversion circuit as a column AD, a pipeline AD, and a successive approximation AD.

The transmitter/receiver 24 outputs digital transmission data, which includes the second signal and a control code with a predetermined image format, via the transmission cable 104 and an input/output pad T1 to the control device 3 in a first period (hereinafter, referred to as "Down Link period"). Moreover, the transmitter/receiver 24 receives digital reception data (hereinafter, referred to as "reception data SYSDATA"), which includes a setting signal, from the control device 3 via the transmission cable 104 and the input/output pad T1 in a second period (hereinafter, referred to as "Up Link period"), and outputs a part of this received reception data SYSDATA to the first generator 25. The transmitter/receiver 24 transmits and receives the transmission data and the reception data SYSDATA in a time division manner via the transmission cable 104 and the one input/output pad T1. Specifically, the transmitter/receiver 24 transmits and receives the transmission data and the reception data SYSDATA in a time division manner while switching between the Up Link period and the Down Link period every line where the first signal is read out from each of the plurality of pixels on one horizontal line in the pixel unit 22. Herein, in addition to the setting signal, the reception data SYSDATA includes, in a predetermined period, clock recovery symbols each having a clock edge for detecting transition timing of data. Moreover, in addition to the digital image signal, the transmission data includes, in a predetermined cycle, the clock recovery symbols each having the clock edge for detecting the transition timing of the data. Such a data format is known as a self-clock signal, and as data including this clock recovery symbol, for example, 8b (bit)/10b (bit) conversion and Manchester encoding, or the like may be used. When T is a cycle of one-bit data, at least one clock recovery symbol (clock transition) is included in 5 T in the 8b/10b conversion and in 2 T in the Manchester encoding. The transmitter/receiver 24 is composed by using a bidirectional driver. For example, for the transmitter/receiver 24, a bidirectional driver is used, which is composed by using a transmission logic circuit, a serializer circuit, a clock multiplier circuit, an amplifier circuit, and the like.

On the reception data SYSDATA input from the transmitter/receiver 24, the first generator 25 generates a first clock signal (hereinafter, referred to as "imager clock signal IMCLK"), and outputs this generated imager clock signal IMCLK to the second generator 26. Specifically, the first generator 25 generates the imager clock signal IMCLK synchronized with the clock edge for detecting the transition timing of the data included in the reception data SYSDATA input from the transmitter/receiver 24, and outputs this generated imager clock signal IMCLK to the second generator 26. Note that a detailed configuration of the first generator 25 will be described later.

On the basis of the imager clock signal IMCLK input from the first generator 25, the second generator 26 generates the imager clock signal IMCLK2 for driving the pixel unit 22 and the AD converter 23 at fixed reference timing, and outputs this imager clock signal IMCLK2 to the pixel unit 22 and the AD converter 23. The second generator 26 is composed by using a timing generator and the like.

(Configuration of Control Device)

Next, a configuration of the control device 3 will be described.

The control device 3 includes a transmitter/receiver 31, a clock data recovery (CDR) unit 32, a third generator 33, and a control unit 34.

The transmitter/receiver 31 transmits digital data, which is input from the control unit 34, via the transmission cable 104 to the imaging device 20, and outputs, to the CDR unit 32, digital data received from the imaging device 20 via the transmission cable 104. For example, for the transmitter/receiver 31, a bidirectional driver is used, which is composed by using a transmission logic circuit, a serializer circuit, a clock multiplier circuit, an amplifier circuit, and the like.

The CDR unit 32 isolates a clock signal and a data signal from transmission data transmitted from the imaging device 20 via the transmission cable 104, and outputs the separated clock signal (imager clock signal IMCLK4) and data signal (reception data SYSDATA) to the control unit 34. The imager clock signal IMCLK4 is a signal based on the imager clock signal IMCLK or the imager clock signal IMCLK2, which operates based on an imager frequency. Accordingly, the control unit 34 can detect a frequency deviation between a frequency of the imager clock signal IMCLK4 included in the transmission data and a frequency of a reference clock signal (hereinafter, referred to as "system clock signal SYSCLK") that serves as a reference for the operations of each unit that constitutes the endoscope system 1, and can output this detection result to the transmitter/receiver 31. The control unit 34 is composed by using a phase frequency comparator or the like.

The third generator 33 generates the system clock signal that serves as a reference for the operations of each unit that constitutes the endoscope system 1, and outputs this system clock signal to the control unit 34. The third generator 33 is composed by using a clock generator such as a crystal oscillator, which operates while taking a highly accurate clock as a reference. In other words, the system clock signal SYSCLK is a signal that continues to maintain high accuracy even if a temperature changes and a power supply voltage fluctuates.

The control unit 34 is composed by using a memory and a processor having any hardware among a digital signal processing (DSP), a field programmable gate array (FPGA)

and a central processing unit (CPU). The control unit 34 controls each unit that constitutes the endoscope system 1. Moreover, the control unit 34 outputs image data to the display device 4 on the basis of the system clock signal SYSCLK input from the third generator 33 and the reception data SYSDATA and the imager clock signal IMCLK4. Specifically, the control unit 34 operates in synchronization with the system clock signal SYSCLK that is input from the third generator 33 and operates at a system frequency. The control unit 34 captures the reception data SYSDATA, which is input from the CDR unit 32, at a clock edge of the imager clock signal IMCLK4, and at the same time, performs retiming for the reception data SYSDATA at a refresh rate based on the system clock signal SYSCLK, and outputs the same as image data to the display device 4. Further, the control unit 34 contains, in the reception data SYSDATA, a digital setting value in which the frequency deviation between the frequency of the imager clock signal IMCLK4 (or IMCLK) detected by the CDR unit 32 and the frequency of the system clock signal SYSCLK becomes small, and then outputs the digital setting value to the transmitter/receiver 31. This setting value includes an error correction code.

(Configuration of First Generator)

Figure 3:
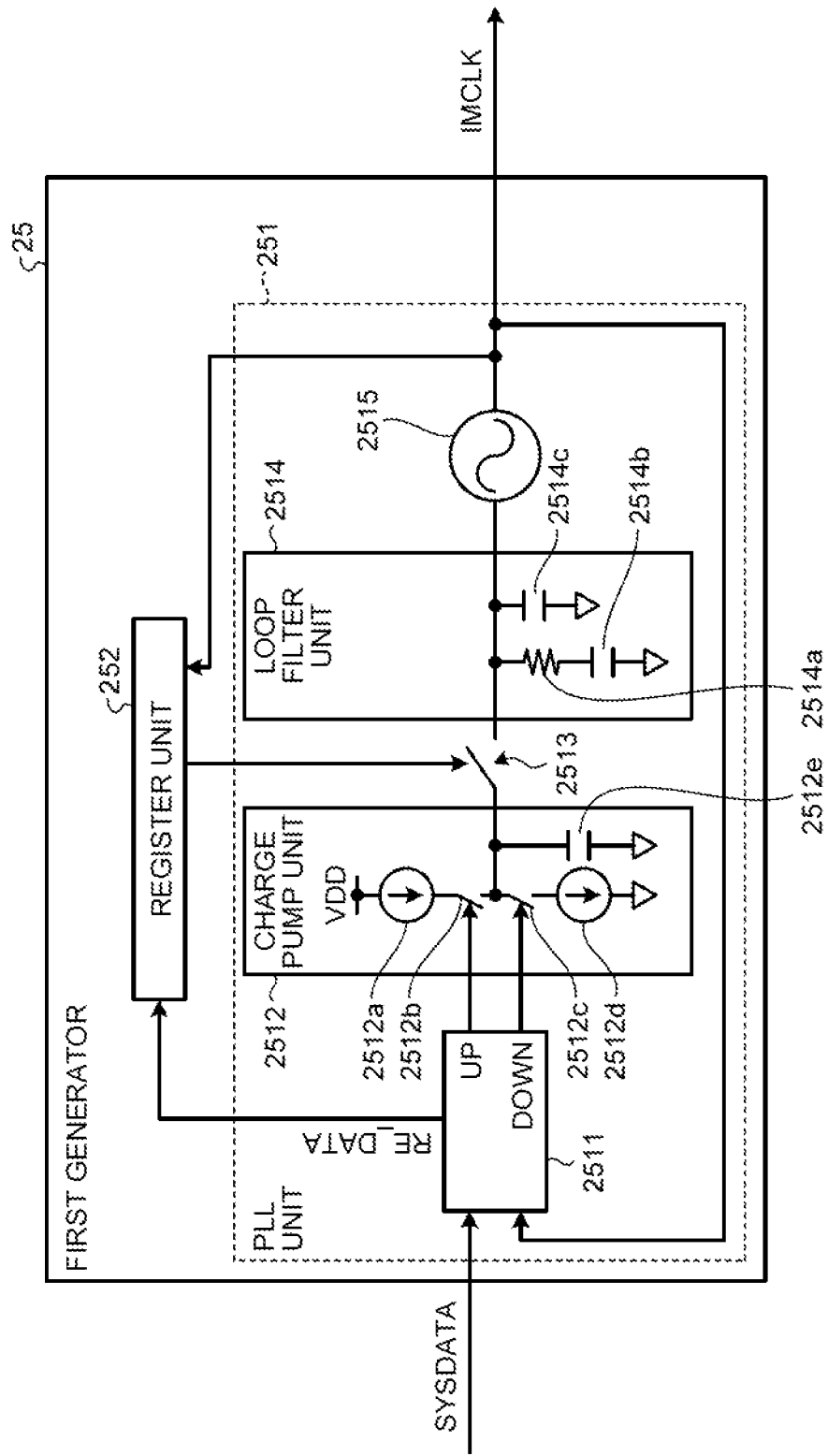
FIG. 3 is a block diagram illustrating a functional configuration of a first generator according to the first embodiment.

Next, a detailed configuration of the first generator 25 will be described. FIG. 3 is a block diagram illustrating a functional configuration of the first generator 25.

As illustrated in FIG. 3, the first generator 25 includes a PLL unit 251 and a register unit 252.

The PLL unit 251 receives input of the reception data SYSDATA from the transmitter/receiver 24, performs phase adjustment for the same so that a phase of a falling clock of the imager clock signal IMCLK becomes the same as a phase of the reception data SYSDATA, and outputs the imager clock signal IMCLK to the second generator 26. The PLL unit 251 includes a phase frequency comparator 2511, a charge pump unit 2512, a switch 2513, a loop filter unit 2514, and a voltage control oscillator 2515.

The phase frequency comparator 2511 samples a value of the reception data SYSDATA at a rising edge timing of the imager clock signal IMCLK, and outputs, to the register unit 252, retiming data RE_DATA synchronized with the imager clock signal IMCLK. The retiming data RE_DATA held in the register unit 252 is used for setting an operation mode in the inside of the image sensor 21, and the like. The phase frequency comparator 2511 is composed by using a flip-flop circuit, a NAND circuit, and the like.

The charge pump unit 2512 includes a constant current source 2512*a*, a switch 2512*b*, a switch 2512*c*, a constant current source 2512*d*, and a capacitor 2512*e*, which are provided between a power supply voltage VDD and a ground GND. The constant current source 2512*a*, the switch 2512*b*, the switch 2512*c* and the constant current source 2512*d* are provided in series between the power supply voltage VDD and the ground GND. In the capacitor 2512*e*, one end thereof is connected to a transmission line to which voltages are output from the constant current source 2512*a*, the switch 2512*b*, the switch 2512*c* and the constant current source 2512*d*, and other end thereof is connected to the ground. When the phase of the imager clock signal IMCLK is delayed with respect to the reception data SYSDATA, and the frequency thereof is low, then such an FMOS 2512*b* is turned on according to an input signal input from the phase frequency comparator 2511, and the charge pump unit 2512 raises a voltage of the input signal and outputs the same. Moreover, when the phase of the imager clock signal IMCLK is delayed with respect to the reception data SYS-DATA, and the frequency thereof is high, then the switch 2512*c* is turned on according to the input signal input from the phase frequency comparator 2511, and the charge pump unit 2512 drops the voltage of the input signal and outputs the same. Further, each of the switch 2512*b* and the switch 2512*c* is composed, for example, by using a MOS-FET or the like.

The switch 2513 switches on and off under control of the register unit 252. In the switch 2513, one end thereof is connected to the charge pump unit 2512, and the other end thereof is connected to the loop filter unit 2514. The switch 2513 is composed, for example, by using a MOS-FET or the like.

The loop filter unit 2514 smooths the voltage of the input signal input via the switch 2513, and outputs the input signal to the voltage control oscillator 2515. The loop filter unit 2514 is composed, for example, by using a low-pass filter or the like. Specifically, the loop filter unit 2514 includes a resistor 2514*a*, a capacitor 2514*b*, and a capacitor 2514*c*. In the resistor 2514*a*, one end thereof is connected to a transmission line that connects the switch 2513 and the voltage control oscillator 2515 to each other, and the other end thereof is connected to the capacitor 2514*b*. In the capacitor 2514*b*, one end thereof is connected to the resistor 2514*a*, and other end thereof is connected to the ground GND. Moreover, in the capacitor 2514*c*, one end thereof is connected to the transmission line that connects the switch 2513 and the voltage control oscillator 2515 to each other, and other end thereof is connected to the ground GND.

The voltage control oscillator 2515 generates the imager clock signal IMCLK having a frequency corresponding to the voltage input from the loop filter unit 2514, outputs this imager clock signal IMCLK to the second generator 26, and outputs the imager clock signal IMCLK to the register unit 252 and the phase frequency comparator 2511.

The register unit 252 sequentially holds the retiming data RE_DATA, which is input from the phase frequency comparator 2511, at timing synchronized with the imager clock signal IMCLK input from the voltage control oscillator 2515, and on the basis of the sequentially held retiming data RE_DATA, uses the imager clock signal IMCLK as setting information for controlling the on/off of the switch 2513, and for the pixel unit 22, the AD converter 23 and the like.

(Operations of First Generator)

Figure 4:
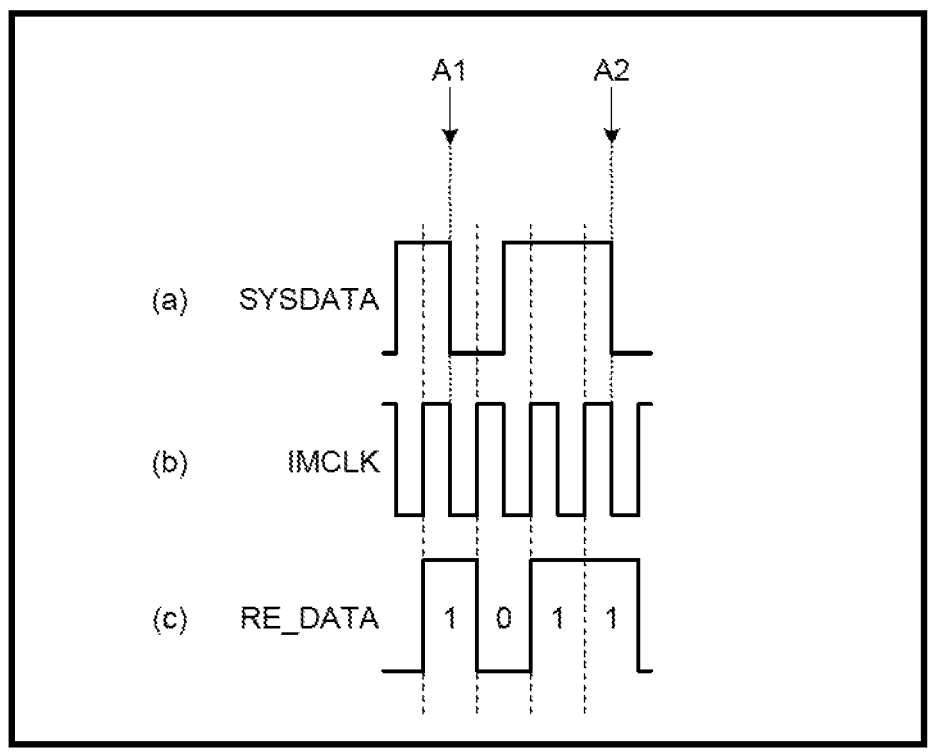
FIG. 4 is a diagram illustrating a timing chart schematically illustrating operations of the first generator according to the first embodiment.

Next, operations of the first generator 25 will be described. FIG. 4 is a diagram illustrating a timing chart schematically illustrating operations of the first generator. In FIG. 4, in order from the top, (a) indicates timing of the reception data SYSDATA, (b) indicates timing of the imager clock signal IMCLK, and (c) indicates timing of the retiming data RE_DATA.

As illustrated in FIG. 4, in the first generator 25, when a line ending command (for example, 1011) is transmitted from the control device 3, the phase frequency comparator 2511 detects the line ending command (for example, 1011) as the retiming data RE_DATA. Specifically, in the first generator 25, the phase frequency comparator 2511 samples the value of the reception data SYSDATA at the rising edge timing (arrow A1 and arrow A2 in FIG. 4) of the imager clock signal IMCLK, and outputs, to the register unit 252, the retiming data RE_DATA synchronized with the imager clock signal IMCLK. At this time, in the first generator 25, the switch 2513 is turned off, and the first generator 25 shifts to the Down Link period while the loop filter unit 2514 keeps the voltage.

In other words, the first generator 25 shifts to the Down Link period while the voltage to be supplied to the voltage control oscillator 2515 is left constant. In this Down Link period, the image sensor 21 outputs the digital image signal to the control device 3 in a state of constantly maintaining an oscillation frequency of the imager clock signal IMCLK.

Subsequently, after outputting, to the control device 3, a digital image signal for one horizontal line in the pixel unit 22, the image sensor 21 outputs, to the control device 3, a command indicating an end of reading such an output amount for one line. At the same timing as this transmission of the command, a part of the data held in the register unit 252 is updated by a mechanism inside a chip (not illustrated), the switch 2513 is turned on (is short-circuited), and the first generator 25 shifts to the Up Link period.

As described above, in the first generator 25, every amount of one horizontal line in the pixel unit 22, a state transition of the operation mode is repeated between the Down Link period and the Up Link period. Thus, even when the oscillation frequency of the imager clock signal IMCLK takes an abnormal value due to a disturbance and the like, and the image signal output by the image sensor 21 is disturbed, a correction command for returning the oscillation frequency of the imager clock signal IMCLK to a normal value can be transmitted every horizontal line in the pixel unit 22. Accordingly, recovery to a normal state can be rapidly performed in comparison with the conventional method in which the correction command can only be transmitted every frame. As a result, data of one whole frame can be prevented from being lost.

(Configuration of Image Format)

Figure 5:
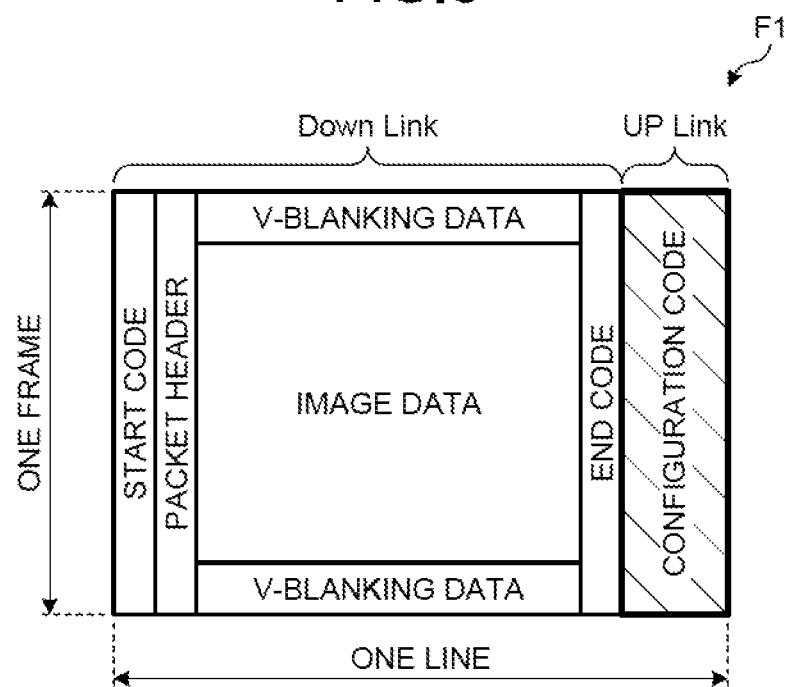
FIG. 5 is a schematic view illustrating a configuration of an image format according to the first embodiment.

Next, a description will be given of a configuration of an image format of the image signal to be output by the image sensor 21. FIG. 5 is a schematic view illustrating the configuration of the image format.

As illustrated in FIG. 5, an image format F1 includes at least a pixel data period and a V-blanking data period. Moreover, every line, the image format F1 includes a start code period, a packet header, an end code, and a configuration code period. Note that, in the image format F1, the pixel data period and the V-blanking data period correspond to a line readout period. Further, in the image format F1, the start code period, the packet header period and the end code period correspond to a service data readout period. Furthermore, in the image format F1, the configuration code period corresponds to a command write period.

The image data period is a digital image signal (second signal) in which a result of performing AD conversion processing for an analog pixel value, which corresponds to an amount of received light accumulated in the pixel unit 22 of the image sensor 21, by the AD converter 23 is transmitted in a Down Link direction (transmission direction to the control device 3) by the transmitter/receiver 24. Moreover, data that constitutes the image data period includes, in a predetermined cycle, a clock recovery symbol for generating reference timing for causing the CDR unit 32 of the control device 3 to detect Down Link data. Such a data format is known as a self-clock signal, and as data including this clock recovery symbol, for example, 8b (bit)/10b (bit) conversion and Manchester encoding, or the like may be used.

The V-blanking data period may be random dummy data, or may be data including a control signal for achieving synchronization with the control device 3. Moreover, each of the image data and the V-blanking data includes, in a predetermined cycle, the clock recovery symbol for generating the reference timing for causing the CDR unit 32 of the control device 3 to detect the Down Link data. Such a data format is known as a self-clock signal, and as data including this clock recovery symbol, for example, 8b (bit)/10b (bit) conversion and Manchester encoding, or the like may be used.

Like the image data and the V-blanking data, the configuration code includes the clock recovery symbol in a predetermined cycle.

According to the image format F1 configured as described above, the transmitter/receiver 24 also transmits data in the Down Link direction in an exposure period of the image sensor 21 or the V-blanking data period provided for frame rate adjustment. Moreover, the control unit 34 transmits data to the image sensor 21 in the configuration code period so that the frequency of the imager clock signal IMCLK becomes the same as the frequency of the system clock signal SYS_CLK during the Up Link period. Then, the PLL unit 251 of the first generator 25 outputs, to the second generator 26, the imager clock signal IMCLK with a frequency instructed by the configuration code.

In accordance with the image format F1 configured as described above, PLL relocking and register setting can be performed every line. Accordingly, in comparison with a conventional technique in which PLL relocking is performed every frame, rapid recovery from an error state can be achieved even when a disturbance noise of an electric scalpel or the like occurs.

In accordance with the first embodiment described above, the transmitter/receiver 24 switches between the Down Link period and the Up Link period every line of the pixel unit 22, and transmits and receives the transmission data and the reception data SYSDATA in a time division manner. Accordingly, the PLL relocking can be performed every line even when the oscillation frequency of the imager clock signal IMCLK takes an abnormal value due to such a disturbance noise of the electric scalpel or the like. Therefore, rapid recovery to a normal state can be achieved in comparison with the conventional method in which the PLL relocking can be performed only every frame. As a result, the data of one whole frame can be prevented from being lost.

Moreover, in accordance with the first embodiment, the transmitter/receiver 24 transmits and receives the transmission data and the reception data SYSDATA via one input/output pad in a time division manner, whereby the transmission of the image data and the reception of the setting signal can be performed by the one transmission cable 104. Accordingly, the insertion portion 100 of the endoscope 2 can be thinned in diameter.

Second Embodiment

Next, a second embodiment will be described. The second embodiment is different from the above-mentioned first embodiment in only the configuration of the first generator 25. A description will be given below of a first generator 25 according to the second embodiment. Note that the same reference numerals will be assigned to the same constituents as those of the endoscope system 1 according to the above-mentioned first embodiment, and a detailed description thereof will be omitted.

(Configuration of First Generator)

Figure 6:
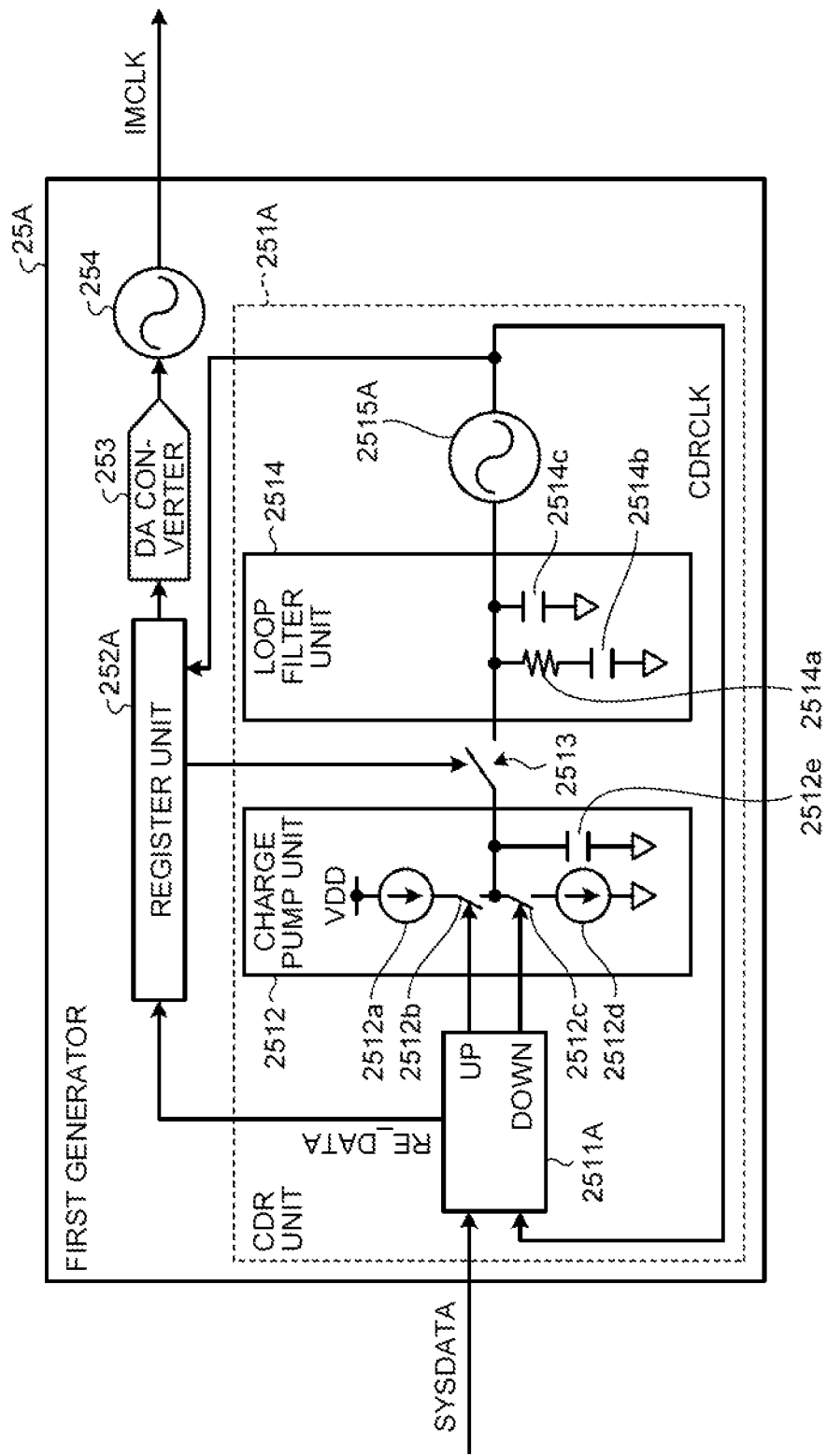
FIG. 6 is a block diagram illustrating a functional configuration of a first generator according to a second embodiment.

FIG. 6 is a block diagram illustrating a functional configuration of the first generator according to the second embodiment. Such a first generator 25A illustrated in FIG. 6 includes a CDR unit 251A, a register unit 252A, a DA converter 253, and a second voltage control oscillator 254.

The CDR unit 251A receives input of the reception data SYSDATA from the transmitter/receiver 24, samples a value of the reception data SYSDATA at rising edge timing of a third clock signal (hereinafter, referred to as "signal CDR-CLK") to be described later, and outputs each of retiming data RE_DATA synchronized with the signal CDRCLK and of the signal CDRCLK to the register unit 252A. The CDR unit 251A includes the charge pump unit 2512 and the loop filter unit 2514 according to the above-mentioned first embodiment, a phase frequency comparator 2511A, and a first voltage control oscillator 2515A. Therefore, a detailed description of the charge pump unit 2512 and the loop filter unit 2514 will be omitted.

The phase frequency comparator 2511A samples the value of the reception data SYSDATA at the rising edge timing of the signal CDRCLK, and outputs, to the register unit 252A, the retiming data RE_DATA synchronized with the signal CDRCLK. The retiming data RE_DATA held in the register unit 252A is used for setting the operation mode in the inside of the image sensor 21, and the like. The phase frequency comparator 2511A is composed by using a flip-flop circuit, a NAND circuit, and the like.

The first voltage control oscillator 2515A generates the signal CDRCLK having a frequency corresponding to the voltage input from the loop filter unit 2514, and outputs this signal CDRCLK to the phase frequency comparator 2511A and the register unit 252A. The signal CDRCLK is used for only determining timing of data extraction of the reception data SYSDATA.

The register unit 252A holds (latches) the retiming data RE_DATA, which is input from the phase frequency comparator 2511A, at timing of synchronizing with the signal CDRCLK input from the first voltage control oscillator 2515A. The register unit 252A controls the on/off of the switch 2513. Upon receiving, as the RE_DATA, the line ending command (for example, 1011) in the Up Link direction from the control device 3, the register unit 252A turns off the switch 2513. Upon sensing the issuance of the line ending command in the Down Link direction from the second generator 26 by a mechanism (not illustrated), the register unit 252A turns on the switch 2513. Moreover, the register unit 252A outputs, to the DA converter 253, a register value corresponding to the retiming data RE_DATA input from the phase frequency comparator 2511A.

The DA converter 253 outputs, to the second voltage control oscillator 254, a voltage corresponding to the register value input from the register unit 252A.

The second voltage control oscillator 254 generates the imager clock signal IMCLK having a frequency corresponding to the voltage input from the DA converter 253, and outputs this imager clock signal IMCLK to the second generator 26.

(Operations of First Generator)

Figure 7:
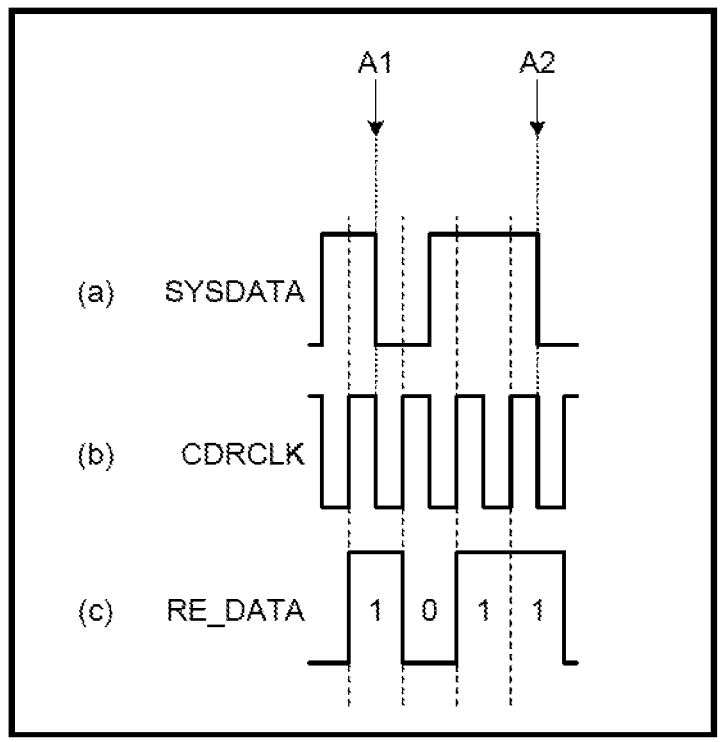
FIG. 7 is a diagram illustrating a timing chart schematically illustrating operations of the first generator according to the second embodiment.

Next, operations of the first generator 25A will be described. FIG. 7 is a diagram illustrating a timing chart schematically illustrating the operations of the first generator 25A. In FIG. 7, in order from the top, (a) indicates timing of the reception data SYSDATA, (b) indicates timing of the CDRCLK, and (c) indicates timing of the retiming data RE_DATA.

As illustrated in FIG. 7, in the first generator 25A, when a line ending command (for example, 1011) is transmitted from the control device 3, the phase frequency comparator 2511 detects the line ending command (for example, 1011) as the retiming data RE_DATA. Specifically, in the first generator 25A, the phase frequency comparator 2511 samples the value of the reception data SYSDATA at the rising edge timing (arrow A1 and arrow A2 in FIG. 7) of the CDRCLK, and outputs, to the register unit 252A, the retiming data RE_DATA synchronized with the CDRCLK. At this time, the switch 2513 is turned off, and the first generator 25A shifts to the Down Link period while the loop filter unit 2514 keeps the voltage.

In other words, the first generator 25A shifts to the Down Link period while the voltage to be supplied to the first voltage control oscillator 2515A is left constant. In this Down Link period, the image sensor 21 outputs the digital image signal to the control device 3 in a state of constantly maintaining an oscillation frequency of the imager clock signal IMCLK. Subsequently, after outputting, to the control device 3, a digital image signal for one horizontal line in the pixel unit 22, the image sensor 21 outputs, to the control device 3, a command indicating an end of reading such an output amount for one line. At the same timing as this transmission of the command, a part of the data held in the register unit 252A is updated by a mechanism inside a chip (not illustrated), and following this update, the switch 2513 is turned on (is short-circuited), and the first generator 25A shifts to the Up Link period. Upon receiving a control command transmitted from the first generator 25A, the control device 3 starts to transmit, to the imaging device 20, the configuration code and the like which are necessary in the Up Link period.

As described above, in the first generator 25A, every amount of one horizontal line in the pixel unit 22, a state transition of the operation mode is repeated between the Down Link period and the Up Link period. Thus, even when the oscillation frequency of the imager clock signal IMCLK takes an abnormal value due to a disturbance and the like, and the image signal output by the image sensor 21 is disturbed, a correction command for returning the oscillation frequency of the imager clock signal IMCLK to a normal value can be transmitted every horizontal line in the pixel unit 22. Accordingly, recovery to a normal state can be rapidly performed in comparison with the conventional method in which the correction command can only be transmitted every frame. As a result, the data of one whole frame can be prevented from being lost.

In accordance with the second embodiment described above, similar effects to those of the above-mentioned first embodiment are provided, and in addition, the oscillation frequency of the imager clock signal IMCLK is controlled against a disturbance noise by a robust digital command. Accordingly, a more stable imager clock signal IMCLK can be supplied.

(First Modification Example of First and Second Embodiments)

Figure 8:
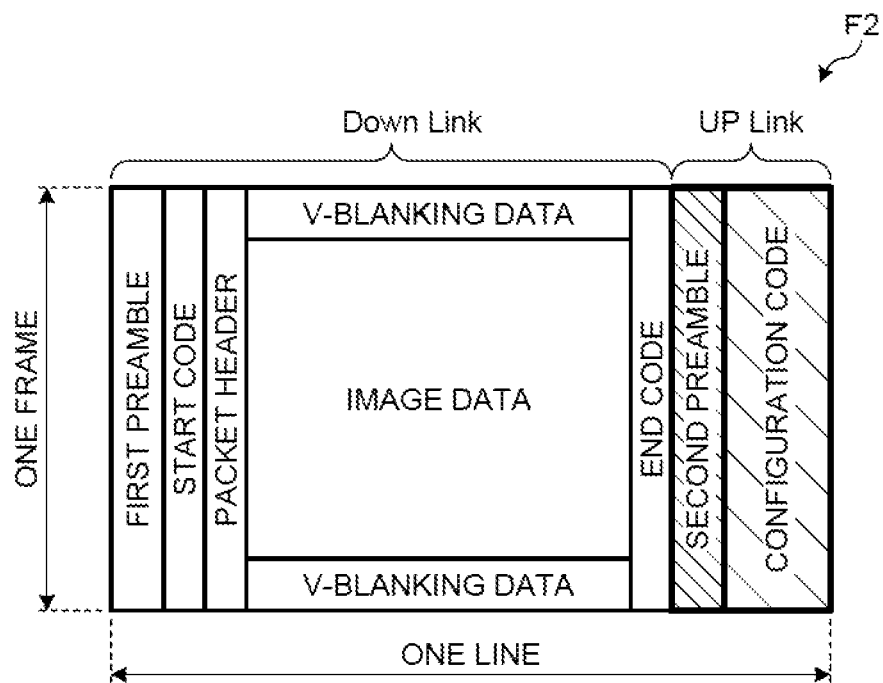
FIG. 8 is a schematic view illustrating an image format according to a first modification example of the first and second embodiments.

Next, a first modification example of the first and second embodiments will be described. FIG. 8 is a schematic view illustrating an image format according to the first modification example of the first and second embodiments.

As illustrated in FIG. 8, in an image format F2, a top of the Down Link period and a top of the Up Link period may be provided with a first preamble period of outputting a first preamble signal and a second preamble period of outputting a second preamble signal, respectively.

The first preamble signal is composed of: an enumeration of specific codes (for example, toggle code 101010101) for use in causing the transmitter/receiver 31 of the control device 3 to synchronize with a clock frequency on the image sensor 21; and increment data (for example, 00, 01, 10, 11) for searching for a data top position.

The second preamble signal is composed of: an enumeration of specific codes (for example, toggle code code) for use in causing the transmitter/receiver 24 of the imaging device 20 to synchronize with a clock frequency on the control device 3; and increment data for searching for a data top position.

Note that, in the image format F2, the first preamble period, the start code period, the packet header period and the end code period correspond to the service data readout period, and the second preamble period and the configuration code period correspond to the command write period.

In accordance with the first modification example of the first and second embodiments, which is described above, similar effects to those of the above-mentioned first and second embodiments are provided. In addition, the reception adjustment in the first generator 25 or 25A or the CDR unit 32 can be rapidly performed by the code portion of the toggle code, which is included in the preamble signal transmitted and received during the preamble period provided every time when the switching of the communication direction is performed. Moreover, by an increment signal portion transmitted and received during the preamble period, it becomes possible to easily detect the top portion of the received data. In other words, the transmission/reception of the digital signal can be surely accomplished both on the control device 3 and on the imaging device 20.

(Second Modification Example of First and Second Embodiments)

Figure 9:
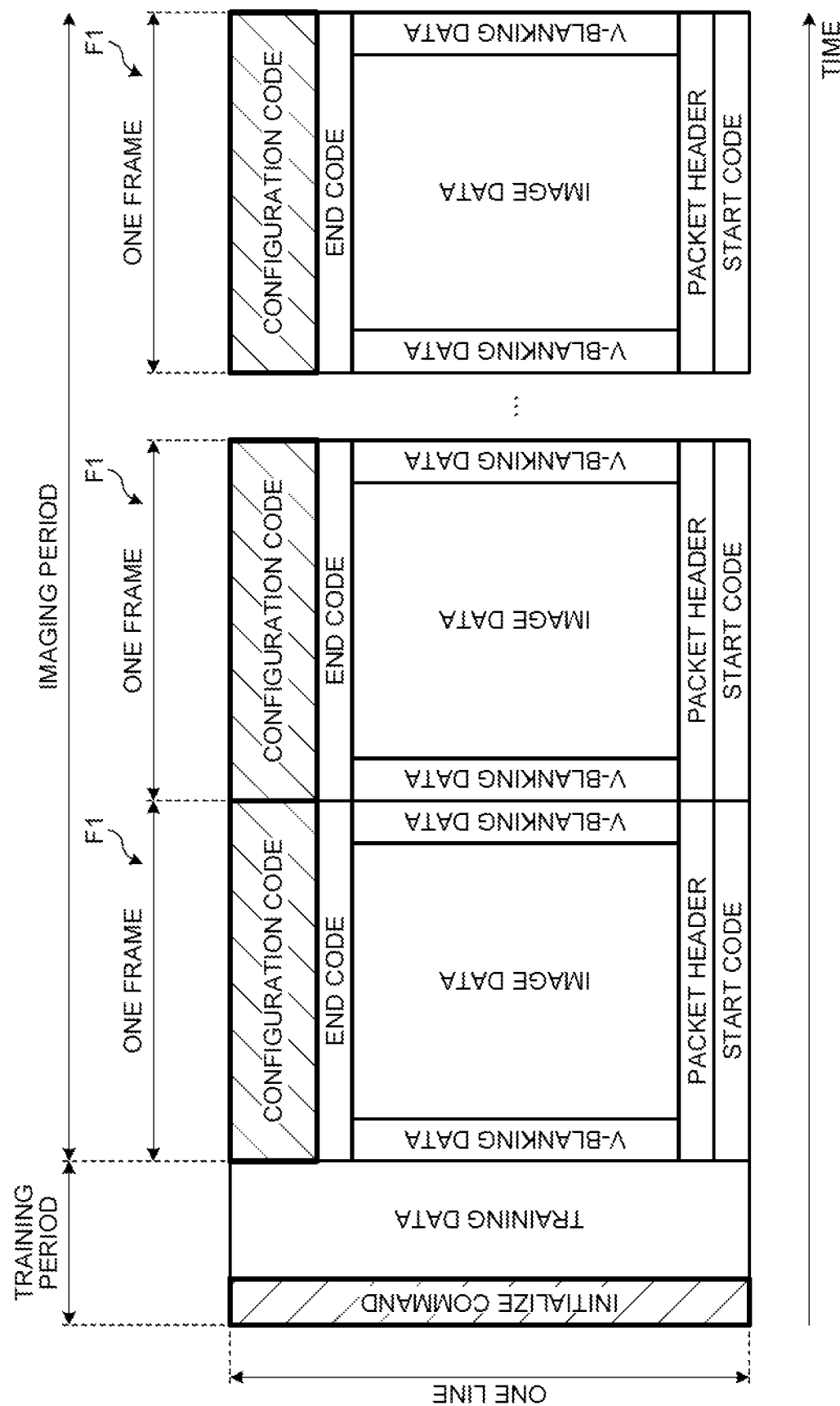
FIG. 9 is a schematic view illustrating an image format according to a second modification example of the first and second embodiments.

Next, a second modification example of the first and second embodiments will be described. FIG. 9 is a schematic view illustrating an image format according to the second modification example of the first and second embodiments.

As illustrated in FIG. 9, the image sensor 21 performs a training period (training phase) while output of at least a predetermined non-image data pattern continues to be output for a predetermined period, and thereafter, performs an imaging period (shooting phase) while input/output of image data, non-image data and command data are repeated every line.

In accordance with the second modification example of the first and second embodiments described above, similar effects to those of the above-mentioned first and second embodiments are provided. In addition, the actual imaging (transmission/reception of the image data) is performed after such an operation condition in which an error rate of the data to be transmitted and received becomes small is established in at least either one of the imaging device 20 and the control device 3 in the training period. Accordingly, error durability of the data to be transmitted and received can be further enhanced.

OTHER EMBODIMENTS

A variety of inventions can be formed by appropriately combining the plurality of constituent elements disclosed in the endoscope systems according to the first and second embodiments of the above-mentioned present disclosure. For example, some constituent elements can be deleted from the entire constituent elements described in the endoscope systems according to the embodiments of the above-mentioned present disclosure. Further, the constituent elements described in the endoscope systems according to the embodiments of the above-mentioned present disclosure may be appropriately combined with one another.

Moreover, in the first and second embodiments of the present disclosure, during all of the line readout period, the service data readout period and the command write period, the transmission data and the reception data may be transmitted and received in a time division manner by differential digital communication.

Further, in the endoscope systems according to the first and second embodiments of the present disclosure, "portion" can be replaced by "means", "circuit" and the like. For example, the control unit can be replaced by control means and a control circuit.

Moreover, a program which the endoscope systems according to the first and second embodiments of the present disclosure are caused to execute is provided by being recorded as file data in an installation-enabled format or an executable format in a computer-readable recording medium such as a CD-ROM, a flexible disk (FD), a CD-R, a digital versatile disk (DVD) a USB medium, and a flash memory.

Further, the program which the endoscope systems according to the first and second embodiments of the present disclosure are caused to execute may be configured to be stored in a computer connected to a network such as the Internet and to be provided by being downloaded via the network.

Note that, in the description of the timing chart in the present description, the temporal order of the respective pieces of processing is explicitly illustrated by using expressions of "first", "thereafter", "subsequently" and the like; however, the order of the pieces of processing required for implementing the present embodiment is not uniquely determined by these expressions. In other words, the processing order in the timing chart described in the present description can be changed within the scope free from contradictory.

Some embodiments of the present application have been described above in detail with reference to the drawings; however, these are illustrations, and other forms subjected to varieties of modifications and improvements on the basis of the knowledge of those skilled in the art, the forms including the modes described in the disclosure columns of the present invention, can implement the present invention.

REFERENCE SIGNS LIST

1 ENDOSCOPE SYSTEM
2 ENDOSCOPE
3 CONTROL DEVICE
4 DISPLAY DEVICE
20 IMAGING DEVICE
21 IMAGE SENSOR
22 PIXEL UNIT
23 AD CONVERTER
24, 31 TRANSMITTER/RECEIVER
25, 25A FIRST GENERATOR
26 SECOND GENERATOR
32, 251A CDR UNIT
33 THIRD GENERATOR
34 CONTROL UNIT
100 INSERTION PORTION
101 DISTAL END
102 PROXIMAL END
103 OPERATING UNIT
104 TRANSMISSION CABLE
251 PLL UNIT
252, 252A REGISTER UNIT
253 DA CONVERTER
254 SECOND VOLTAGE CONTROL OSCILLATOR
2511 PHASE FREQUENCY COMPARATOR
2512 CHARGE PUMP UNIT
2512a, 2512d CONSTANT CURRENT SOURCE
2512b, 2512c, 2513 SWITCH 2512e, 2514b, 2514c CAPACITOR
2514 LOOP FILTER UNIT
2514a RESISTOR
2515
2515A FIRST VOLTAGE CONTROL OSCILLATOR
F1, F2 IMAGE FORMAT
T1 INPUT/OUTPUT PAD

The invention claimed is:

1. An image sensor comprising:
a pixel unit including a plurality of pixels arranged in a two-dimensional matrix, each of the plurality of pixels being configured to generate, by receiving light, a first signal corresponding to an amount of the received light, and output the first signal;
an AD converter configured to convert the first signal output from each of the plurality of pixels into a digital second signal by performing AD conversion processing for the first signal, and output the second signal;
a transmitter/receiver configured to transmit and receive, in a time division manner, transmission data including at least the second signal in a first period, and reception data input from an outside in a second period, the reception data including a setting signal and a clock recovery symbol having a clock edge for detecting transition timing of data;
a first generator configured to generate a first clock signal synchronized with the clock edge included in the reception data; and
a second generator configured to generate, based on the first clock signal, a second clock signal for driving the pixel unit and the AD converter at fixed reference timing, and output the second clock signal to the pixel unit and the AD converter, wherein
the first generator includes:
 a chase frequency comparator configured to output an input signal indicating a comparison result of comparing the first clock signal and the reception data with each other;
 a charge pump unit configured to, based on the input signal input from the phase frequency comparator, adjust a voltage of the input signal and output the input signal;
 a loop filter unit configured to smooth the voltage of the input signal input from the charge pump unit and outputs the input signal;
 a first voltage control oscillator configured to generate and output a third clock signal having a frequency corresponding to the input signal input from the loop filter unit;
 a DA converter configured to perform DA conversion processing for the third clock signal input from the first voltage control oscillator and output the third clock signal; and
 a second voltage control oscillator configured to generate and output the first clock signal having a frequency corresponding to a voltage of the analog third clock signal input from the DA converter, and
the transmitter/receiver is configured to switch between the first period and the second period every horizontal line in the pixel unit, and transmit and receive the transmission data and the reception data in a time division manner.

2. The image sensor according to claim 1, wherein the transmitter/receiver is configured to transmit and receive the transmission data and the reception data in a time division manner via one input/output pad.

3. The image sensor according to claim 1, wherein the first generator includes:
a phase frequency comparator configured to output an input signal indicating a comparison result of comparing the first clock signal and the reception data with each other;
a charge pump unit configured to, based on the input signal input from the phase frequency comparator, adjust a voltage of the input signal and output the input signal;
a loop filter unit configured to smooth the voltage of the input signal input from the charge pump unit and output the input signal; and
a first voltage control oscillator configured to generate and output the first clock signal having a frequency corresponding to the voltage of the input signal input from the loop filter unit.

4. The image sensor according to claim 3, wherein the setting signal includes a frequency control signal of the second clock signal, and
the transmission data includes the second signal and a preamble signal to be output at earlier timing than the second signal.

5. The image sensor according to claim 3, wherein the transmission data includes an image format, and
the image format has a configuration code period at least every line.

6. An endoscope comprising:
the image sensor according to claim 1; and
an insertion portion having a distal end inserted into a subject, wherein the image sensor is provided on the distal end.

7. A control device to which an endoscope is detachably connected, the endoscope including an image sensor provided on a distal end of an insertion portion insertable into a subject, the control device comprising:
a transmitter/receiver configured to transmit and receive transmission data and reception data in a time division manner, wherein
the transmission data passes via one transmission cable and is transmitted at least from the image sensor in a first period, the transmission data including image data, non-image data, and a clock recovery symbol having a clock edge for detecting transition timing of data, and
the reception data being received by the image sensor and including a setting signal and a clock recovery symbol having a clock edge for detecting transition timing of data.

8. The control device according to claim 7, further comprising:
a third generator configured to generate a reference clock signal serving as a reference of an operation of the control device; and
a control unit configured to output the image data to a display device based on the reference clock signal and a first clock signal generated in synchronization with the clock edge included in the reception data.

* * * * *